(12) United States Patent
Moore

(10) Patent No.: US 10,677,943 B2
(45) Date of Patent: Jun. 9, 2020

(54) SYSTEM AND METHOD FOR MONITORING A COMPUTED TOMOGRAPHY IMAGING SYSTEM

(71) Applicant: MORPHO DETECTION, LLC, Newark, CA (US)

(72) Inventor: Jared William Moore, Oakland, CA (US)

(73) Assignee: Smiths Detection, LLC, Newark, CA (US)

( * ) Notice: Subject to any disclaimer, the term of this patent is extended or adjusted under 35 U.S.C. 154(b) by 701 days.

(21) Appl. No.: 15/381,244

(22) Filed: Dec. 16, 2016

(65) Prior Publication Data

US 2018/0172854 A1 Jun. 21, 2018

(51) Int. Cl.
| | |
|---|---|
| *G01T 7/00* | (2006.01) |
| *A61B 6/03* | (2006.01) |
| *G01N 23/046* | (2018.01) |
| *A61B 6/00* | (2006.01) |
| *G01T 1/29* | (2006.01) |
| *G01V 5/00* | (2006.01) |

(52) U.S. Cl.
CPC .............. *G01T 7/00* (2013.01); *A61B 6/032* (2013.01); *A61B 6/586* (2013.01); *G01N 23/046* (2013.01); *G01T 1/2985* (2013.01); *G01V 5/005* (2013.01); *A61B 6/035* (2013.01)

(58) Field of Classification Search
CPC ...... A61B 6/03; G01N 23/046; G01T 1/2985; G01T 7/00; G01V 5/005
See application file for complete search history.

(56) References Cited

U.S. PATENT DOCUMENTS

| 4,991,150 A | 2/1991 | Wixom | |
|---|---|---|---|
| 10,039,505 B2* | 8/2018 | Bailey | ........................ A61B 6/56 |
| 10,176,736 B2* | 1/2019 | Chaji | ...................... G09G 3/006 |
| 10,213,626 B2* | 2/2019 | Balakin | ................ A61N 5/1077 |
| 10,342,506 B2* | 7/2019 | Beyerlein | ............... A61B 6/542 |
| 2003/0047686 A1* | 3/2003 | Fries | ...................... G01T 1/2985 |
| | | | 250/363.03 |
| 2004/0125908 A1* | 7/2004 | Cesmeli | .................. A61B 6/032 |
| | | | 378/4 |
| 2006/0210013 A1* | 9/2006 | Kasuya | ................... A61B 6/035 |
| | | | 378/4 |

(Continued)

*Primary Examiner* — David J Makiya
*Assistant Examiner* — Soorena Kefayati
(74) *Attorney, Agent, or Firm* — Armstrong Teasdale LLP

(57) ABSTRACT

A diagnostic system for monitoring a status of a CT system includes at least one radiation detector configured to monitor a CT component and generate signals representing measurement data associated with the CT component. The system also includes a diagnostic computer device in communication with the detector. The device is configured to receive an electrical signal from the detector and identify a first frequency in the electrical signal. The device is also configured to compare the first frequency in the electrical signal to a first reference frequency stored in memory. The first reference frequency is at least partially indicative of a first mechanical status of the CT component. The device is further configured to determine that the first frequency in the electrical signal is substantially similar to the first reference frequency and, in response, determine that the CT system has the first mechanical status.

27 Claims, 11 Drawing Sheets

(56) References Cited

U.S. PATENT DOCUMENTS

| | | | |
|---|---|---|---|
| 2007/0067678 A1* | 3/2007 | Hosek | G05B 23/0235 714/25 |
| 2008/0205446 A1* | 8/2008 | Popescu | A61B 6/56 370/473 |
| 2009/0243841 A1* | 10/2009 | Alsafadi | A61B 5/1114 340/539.22 |
| 2012/0236999 A1* | 9/2012 | Altvater | A61B 6/4441 378/196 |
| 2012/0294412 A1* | 11/2012 | Baumann | A61B 6/44 378/4 |
| 2013/0082712 A1* | 4/2013 | Stocker | A61B 5/055 324/322 |
| 2013/0129036 A1* | 5/2013 | Baumann | A61B 6/44 378/4 |
| 2013/0184537 A1* | 7/2013 | Konuma | A61B 5/0033 600/300 |
| 2013/0259199 A1* | 10/2013 | Ueji | G01N 23/20008 378/70 |
| 2013/0322597 A1* | 12/2013 | Uchiyama | G01T 1/17 378/62 |
| 2014/0003582 A1* | 1/2014 | Poulo | A61B 6/032 378/91 |
| 2014/0016758 A1* | 1/2014 | Theiss | A61B 6/035 378/197 |
| 2014/0278261 A1* | 9/2014 | Walerow | G01T 1/02 702/189 |
| 2015/0066431 A1* | 3/2015 | Zheng | A61B 6/032 702/183 |
| 2015/0169393 A1* | 6/2015 | Shibuya | G06F 11/00 702/182 |
| 2015/0185107 A1* | 7/2015 | Lou | G01M 1/36 73/468 |
| 2015/0363925 A1* | 12/2015 | Shibuya | G05B 23/0235 345/440 |
| 2016/0077124 A1* | 3/2016 | Karr | G01T 7/00 250/363.03 |
| 2016/0097638 A1* | 4/2016 | Fedigan | G01C 9/06 324/71.1 |
| 2016/0305895 A1* | 10/2016 | Ferro | G06T 7/00 |
| 2016/0327625 A1* | 11/2016 | Vermiglio | A61B 6/032 |
| 2017/0315516 A1* | 11/2017 | Kozionov | G01H 1/003 |

* cited by examiner

SYSTEM AND METHOD FOR MONITORING A COMPUTED TOMOGRAPHY IMAGING SYSTEM

BACKGROUND

The embodiments described herein relate generally to computed tomography (CT) imaging systems, and more particularly, to rotating gantry systems for use in CT imaging systems.

Some known CT imaging systems include a gantry having an x-ray source and one or more x-ray detectors. The gantry has an opening defined therein, and rotates about a central rotational axis to capture imaging data on an object positioned within the gantry opening using the x-ray source and x-ray detectors. The gantry is typically mounted to the CT imaging system by a bearing system that enables the gantry to rotate.

The gantry is often rotated at significant speeds to facilitate the collection of accurate imaging data during a helical or circular scan of an object. As a result, at least some known CT imaging systems utilize costly and complex bearing systems to enable gantry rotation. For example, some known CT imaging systems utilize slew- or roller-type bearing assemblies having numerous rolling elements disposed between two bearing rings. Such bearing assemblies often utilize a large number of rolling elements to enable high-speed rotation of gantry. Additionally, the components of such bearing assemblies are often of significant size and, consequently, of significant cost. For example, bearing rings used in some gantry bearing assemblies have a diameter in excess of a meter, i.e., over three feet. As a result, repairing and replacing components on gantry bearing assemblies often requires significant time and cost.

Additionally, known methods of monitoring the mechanical status of a CT system require the installation of additional sensors (e.g., accelerometers, tachometers), field visits by service technicians, or the partial disassembly of the system (e.g., bearing removal) to troubleshoot and/or verify a suspected problem. In some instances, a mechanical issue is only known once the issue becomes significant enough to make an audible sound during operation. In some cases, the longer the issue persists, the more costly it is to fix the issue, as increased stress on one component leads to anomalous operation of the component and increased stress on other mechanical components in the system.

BRIEF DESCRIPTION

In one aspect, a diagnostic system for monitoring a status of a computed tomography (CT) system is provided. The diagnostic system includes at least one radiation detector element configured to monitor a CT component and generate signals representing measurement data associated with the CT component. The diagnostic system also includes a diagnostic computer device including a processor and a memory coupled to the processor. The diagnostic computer device is in communication with the at least one radiation detector element. The diagnostic computer device is configured to receive an electrical signal from the at least one radiation detector element and identify a first frequency in the electrical signal. The diagnostic computer device is also configured to compare the first frequency in the electrical signal to a first reference frequency stored in the memory device. The first reference frequency is at least partially indicative of a first mechanical status of the CT component. The diagnostic computer device is further configured to determine that the first frequency in the electrical signal is substantially similar to the first reference frequency, and, in response to determining that the first frequency is substantially similar to the first reference frequency, determine that the CT system has the first mechanical status.

In another aspect, a computed tomography (CT) system is provided. The CT system includes a gantry configured to rotate. The gantry includes at least one gantry bearing frame member and a gantry bearing coupled to the gantry bearing frame. The gantry also includes at least one radiation detector element coupled to the at least one gantry bearing frame member. The at least one radiation detector element is configured to monitor the gantry bearing and configured to generate signals representing measurement data associated with the gantry bearing. The CT system also includes a diagnostic computer device including a processor and a memory coupled to the processor. The diagnostic computer device is in communication with the at least one radiation detector element. The diagnostic computer device is configured to receive an electrical signal from the at least one radiation detector element and identify a first frequency in the electrical signal. The diagnostic computer device is also configured to compare the first frequency in the electrical signal to a first reference frequency stored in the memory device. The first reference frequency is at least partially indicative of a first mechanical status of the CT component. The diagnostic computer device is further configured to determine that the first frequency in the electrical signal is substantially similar to the first reference frequency, and, in response to determining that the first frequency is substantially similar to the first reference frequency, determine that the CT system has the first mechanical status.

In yet a further aspect, a method of monitoring a computed tomography (CT) system is provided. The CT system includes at least one CT component and a diagnostic system including at least one radiation detector element. The diagnostic system is coupled to the at least one CT component. The method includes receiving, by the diagnostic system, an electrical signal from the at least one radiation detector element. The method also includes identifying, with the diagnostic system, a first frequency in the electrical signal. The method further includes comparing, with the diagnostic system, the first frequency in the electrical signal to a first reference frequency stored in a memory device. The first reference frequency is at least partially indicative of a first mechanical status of the at least of CT component. The method also includes determining, with the diagnostic system, that the first frequency in the electrical signal is substantially similar to the first reference frequency. The method further includes in response to determining that the first frequency is substantially similar to the first reference frequency, determining, with the diagnostic system, that the CT system has the first mechanical status.

DRAWINGS

FIG. 1 is a block diagram of an exemplary computing device;

FIG. 2 is a block diagram of a portion of an exemplary monitoring and control system that may include the computing device shown in FIG. 1;

FIG. 3 is a schematic perspective view of an exemplary computed tomography (CT) imaging system that may use the computing device shown in FIG. 1 and the monitoring and control system shown in FIG. 2;

FIG. 4 is a schematic diagram of the CT imaging system shown in FIG. 3;

FIG. 5 is a schematic front view of an exemplary rotatable gantry that may be used with the CT imaging system shown in FIGS. 3 and 4;

FIG. 6 is a schematic diagram of an exemplary diagnostic system for the CT imaging system (shown in FIGS. 3 and 5) integrated with the monitoring and control system shown in FIG. 2;

FIG. 7 is an exemplary method of monitoring the CT imaging system shown in FIGS. 3 and 4 with the monitoring and control system shown in FIG. 2;

FIG. 8 is a flow chart of an exemplary process that can be used to implement the method shown in FIG. 7 using the diagnostic system shown in FIG. 6;

FIG. 9 is a graphical representation of raw acceleration data in the time domain received from one radiation detector element of the CT imaging system (shown in FIGS. 3 and 5);

FIG. 10 is a graphical representation of the raw acceleration data shown in FIG. 9 transformed into the frequency domain; and FIG. 11 is a graphical representation of a plurality of indications from radiation detector elements found in a fleet of CT imaging systems (shown in FIGS. 3 and 5).

DETAILED DESCRIPTION

Figure 1:
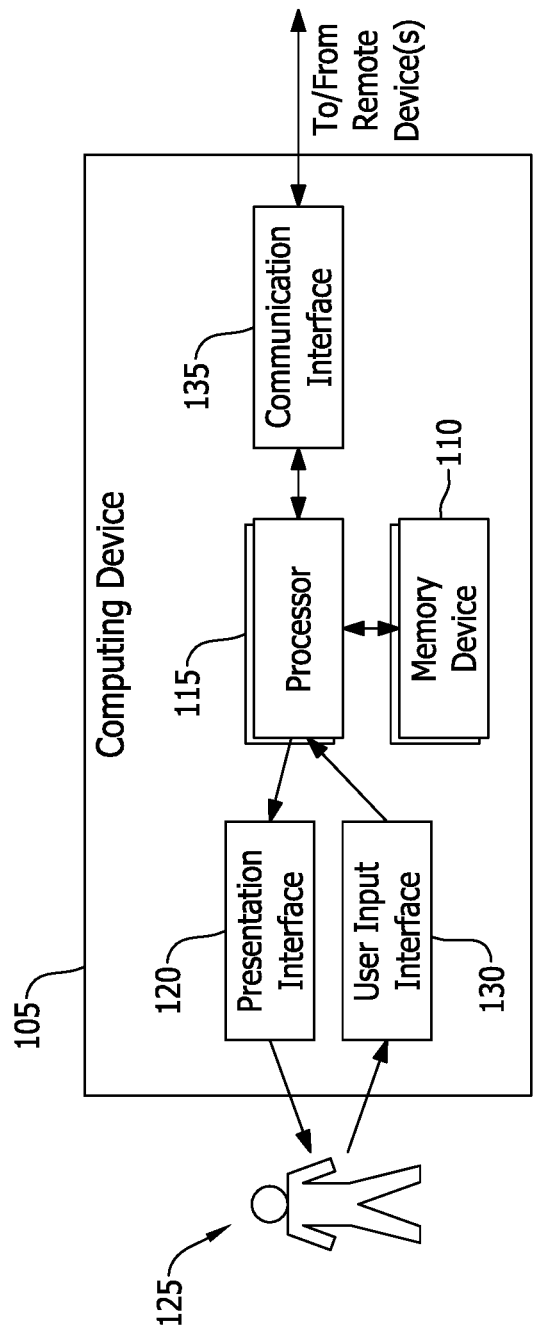
FIGS. 1-11 show exemplary embodiments of the systems and methods described herein.

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random access memory (RAM), and/or a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

The embodiments described herein provide a cost-effective system and method for improving diagnostics of mechanical devices within computed tomography (CT) imaging systems. The systems and methods described herein use a diagnostic system for monitoring a mechanical status, e.g., bearing vibration of a CT imaging system using a plurality of radiation detector elements that are already installed and used for detecting the x-rays that will be used for imaging. The diagnostic system identifies a first frequency through the radiation detector elements and compares the first frequency to a first stored reference frequency in association with a first mechanical status of the CT imaging system. Further, the diagnostic system determines that the first frequency has a threshold level of similarity to the first reference frequency, and in response to determining that the first frequency has the threshold level of similarity of the first reference frequency, determines that the CT imaging system has the first mechanical status.

In some implementations, the diagnostic system is further configured to determine that the CT imaging system may have a defective bearing, based on the first frequency. Further, in some implementations, the CT imaging system includes a rotatable gantry and the diagnostic system is further configured to determine a mass imbalance associated with the rotatable gantry, based on the first frequency. Additionally, in some implementations, the diagnostic system is further configured to receive the electrical signals from the radiation detector elements when the CT imaging system is performing an offset scan, for example a periodic calibration scan. Moreover, in some implementations, the diagnostic system is configured to calculate a speed of rotation of the rotatable gantry.

Further, in some implementations, the diagnostic system is configured to detect a change in an offset current associated with the each of the radiation detector elements. Also, in some implementations, the diagnostic system is further configured to determine a magnitude of the first frequency and calculate a stress on each radiation detector element. Moreover, in some embodiments, the first reference frequency is one of a plurality of stored reference frequencies, and the diagnostic system is further configured to determine a respective level of similarity between the first frequency and each of the plurality of reference frequencies.

Since the embodiments described herein are substantially software-based, the software may be retroactively deployed on existing CT imaging systems. Therefore, the utilization of the current hardware configuration saves a substantial amount of time and expense in the retrofit activities. In addition, the embodiments described herein facilitate diagnostic monitoring such that maintenance schedules may be adjusted based on the material condition data obtained. For example, little to no change in bearing vibration signatures over a predetermined period of time facilitates postponing costly maintenance activities.

FIG. 1 is a block diagram of an exemplary computing device 105 that may be used to perform monitoring and/or control of a computed tomography (CT) imaging system (not shown in FIG. 1) and, more specifically, facilitate performing diagnostics of mechanical devices (not shown in FIG. 1) within the CT imaging system. Also, in the exemplary embodiment, computing device 105 monitors and/or controls any piece of equipment, any system, and any process associated with the CT imaging system, e.g., without limitation, gantry rotation drive motors, x-ray generation tubes, radiation detector elements, and various monitoring devices (neither shown in FIG. 1) for the CT imaging system. Computing device 105 includes a memory device 110 and a processor 115 operatively coupled to memory device 110 for executing instructions. In some embodiments, executable instructions are stored in memory device 110. Computing device 105 is configurable to perform one or more operations described herein by programming processor 115. For example, processor 115 may be programmed by encoding an operation as one or more executable instructions and providing the executable instructions in memory device 110. In the exemplary embodiment, memory device 110 is one or more devices that enable storage and retrieval of information such as executable instructions and/or other data. Memory device 110 may include one or more computer readable media.

Memory device 110 may be configured to store operational measurements including, without limitation, real-time and historical mechanical diagnostic data of the CT imaging system and/or any other type data. Also, memory device 110 includes, without limitation, sufficient data, algorithms, and commands to facilitate monitoring and control of the components within the associated CT imaging system.

In some embodiments, computing device 105 includes a presentation interface 120 coupled to processor 115. Presentation interface 120 presents information, such as a user interface and/or an alarm, to a user 125. In some embodiments, presentation interface 120 includes one or more display devices. In some embodiments, presentation interface 120 presents an alarm associated with the associated electric power distribution system being monitored and controlled, such as by using a human machine interface (HMI) (not shown in FIG. 1). Also, in some embodiments, computing device 105 includes a user input interface 130. In the exemplary embodiment, user input interface 130 is coupled to processor 115 and receives input from user 125.

A communication interface 135 is coupled to processor 115 and is configured to be coupled in communication with one or more other devices, such as a sensor or another computing device 105, and to perform input and output operations with respect to such devices while performing as an input channel. Communication interface 135 may receive data from and/or transmit data to one or more remote devices. For example, a communication interface 135 of one computing device 105 may transmit an alarm to the communication interface 135 of another computing device 105.

In the exemplary embodiment, control and monitoring of a CT imaging system is performed with local control devices, i.e., a localized computing device 105. Alternatively, control and monitoring of such CT imaging systems may be performed as a portion of a larger, more comprehensive system.

Figure 2:
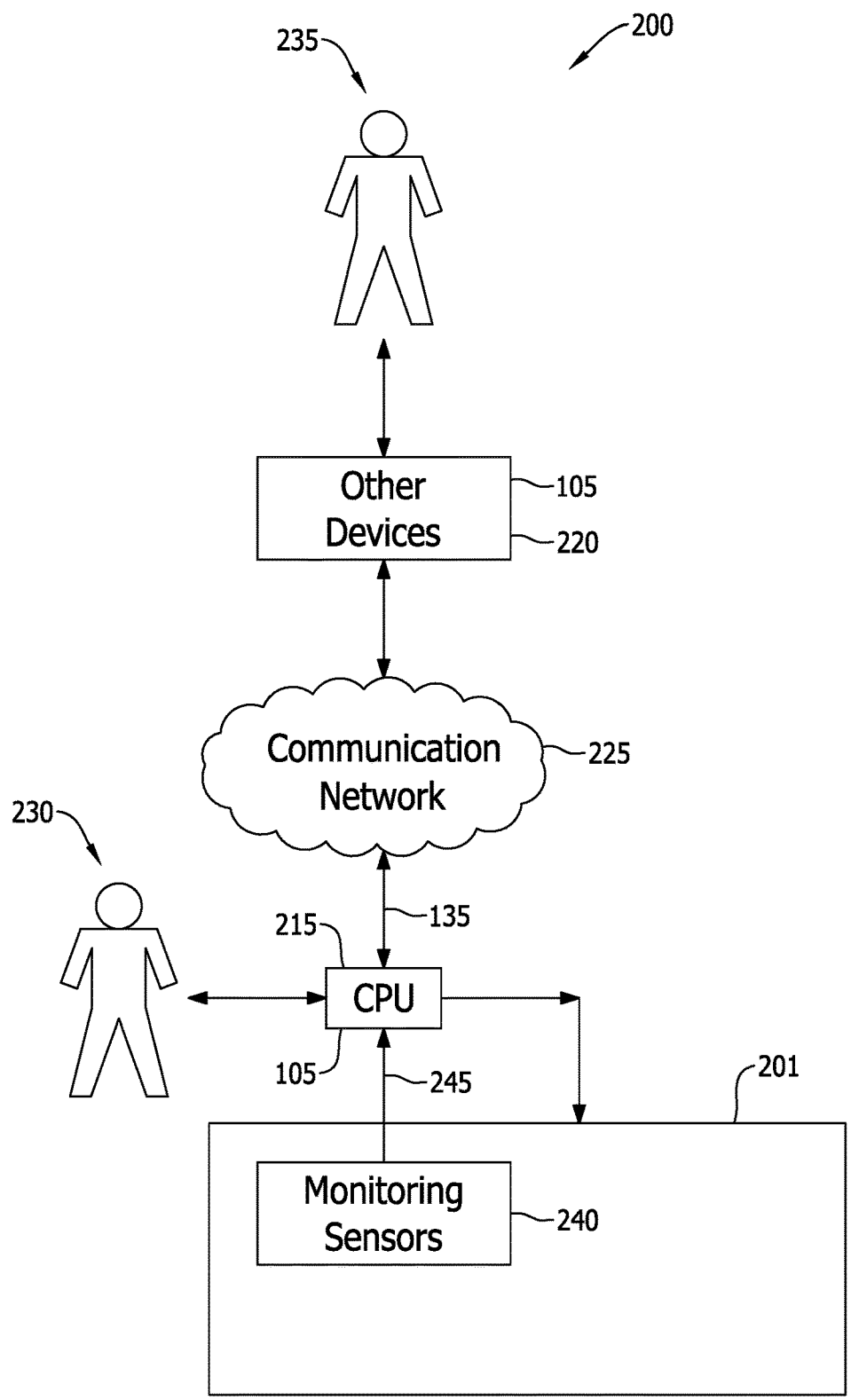

FIG. 2 is a block diagram of a portion of a CT monitoring and control system 200 that may be used to monitor and control at least a portion of a CT imaging system 201. CT monitoring and control system 200 includes at least one central processing unit (CPU) 215 configured to execute monitoring and control algorithms and monitoring and control logic. CPU 215 may be coupled to other devices 220 via a communication network 225, where, in some embodiments, communication network 225 includes the Internet. In some embodiments, CPU 215 is a computing device 105. In other embodiments, CPU 215 is a controller.

CPU 215 interacts with a first operator 230, e.g., without limitation, via user input interface 130 and/or presentation interface 120 (both shown in FIG. 1). In one embodiment, CPU 215 presents information about CT imaging system 201, such as alarms, to operator 230. Other devices 220 interact with a second operator 235, e.g., without limitation, via user input interface 130 and/or presentation interface 120. For example, other devices 220 present alarms and/or other operational information to second operator 235. As used herein, the term "operator" includes any person in any capacity associated with operating and maintaining CT imaging system 201, including, without limitation, imaging technicians, maintenance technicians, doctors, and nurses.

In some embodiments, other devices 220 include one or more storage devices that are any computer-operated hardware suitable for storing and/or retrieving data, for example, and without limitation, multiple storage units such as hard disks or solid state disks in a redundant array of inexpensive disks (RAID) configuration, a storage area network (SAN), and/or a network attached storage (NAS) system.

CT imaging system 201 includes one or more monitoring sensors 240 coupled to CPU 215 through at least one input channel 245. Monitoring sensors 240 collect operational measurements including, without limitation, x-ray source voltages and currents, radiation detector elements, and diagnostics of mechanical devices of CT imaging system 201. Monitoring sensors 240 repeatedly, e.g., periodically, continuously, and/or upon request, transmit operational measurement readings at the time of measurement. CPU 215 receives and processes the operational measurement readings. In one embodiment, such data may be transmitted across network 225 and may be accessed by any device capable of accessing network 225 including, without limitation, desktop computers, laptop computers, and personal digital assistants (PDAs) (neither shown).

In some embodiments, some components described for FIG. 2 may be used with the stand-alone computing device 105 (as shown in FIG. 1), e.g., without limitation, monitoring sensors 240. In such embodiments, computing device 105 includes, without limitation, sufficient data, algorithms, and commands to independently facilitate control and monitoring of CT imaging system 201 as described herein, thereby embodying a significant portion of CT monitoring and control system 200 substantially within stand-alone computing device 105.

Figure 3:
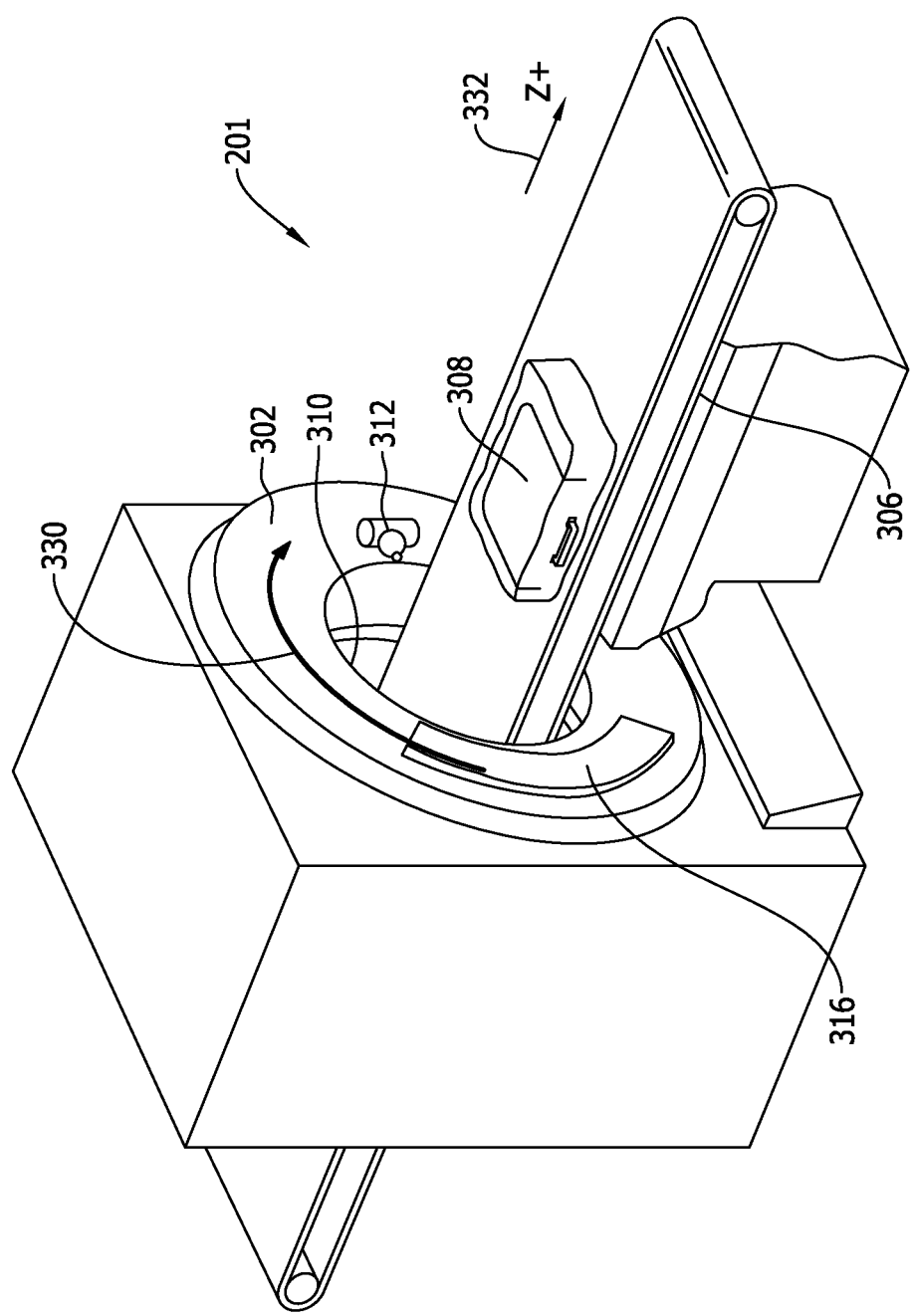
Figure 4:
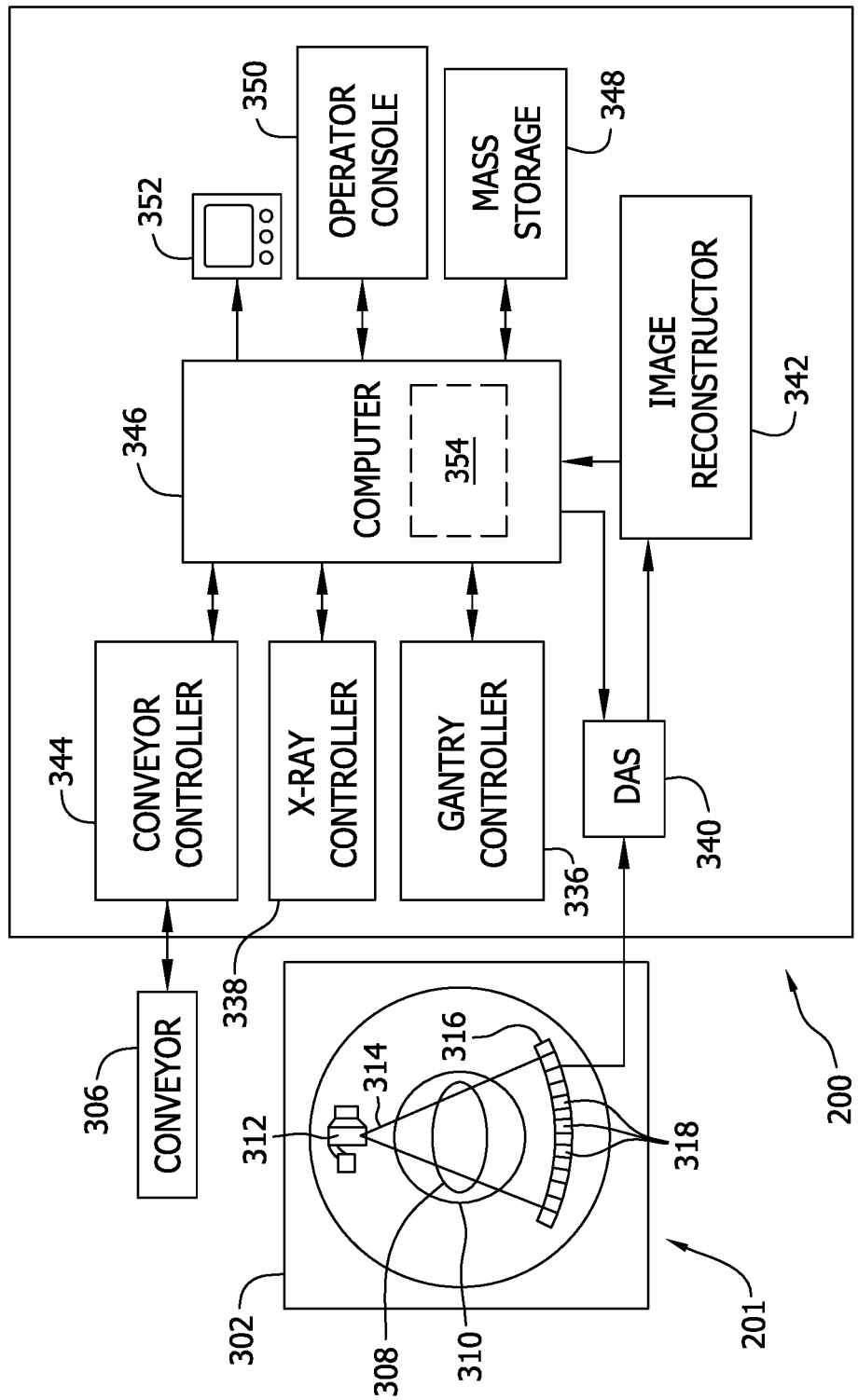

FIG. 3 is a schematic perspective view of computed tomography (CT) imaging system 201 that uses computing device 105 (shown in FIGS. 1 and 4) and monitoring and control system 200 (shown in FIGS. 2 and 4). FIG. 4 is a schematic diagram of CT imaging system 201 including monitoring and control system 200. Referring to FIGS. 3 and 4, CT imaging system 201 includes a rotatable gantry 302, which is representative of a CT scanner, a monitoring and control system 200, and a motorized conveyor belt 306 for positioning a container 308 (or, in some embodiments, a patient), such as a piece of luggage or a shipping container or package, in a gantry opening 310 defined through gantry 302. Gantry 302 includes an x-ray source 312 that projects a fan beam of polychromatic x-rays 314 toward a detector array 316 on the opposite side of gantry 302. X-ray source 312 includes an x-ray tube (not shown) that includes and anode and a cathode (e.g., without limitation, tungsten filament) (neither shown) coupled to an electric power source (not shown) that receives a voltage and a current that is controlled by a processing device (described further below).

Detector array 316 includes a plurality of radiation detector elements 318, which are shown in more detail in FIG. 5 and discussed further below. Detector elements 318 are radiation detectors that each produce a signal having a magnitude that represents and is dependent on the intensity of the attenuated x-ray beam after it has passed through container 308 being imaged. During a helical scan that acquires x-ray projection data, gantry 302 along with x-ray source 312 and detector array 316 rotate within a plane in the direction of arrow 330 and around container 308 about a center of rotation, while container 308 is moved through gantry 302 in a z-direction 332 perpendicular to the plane of rotation. In the exemplary embodiment, detector array 316 includes a plurality of detector rings each having a plurality of detector elements 318, the detector rings having an angular configuration corresponding to x-ray source 312. Monitoring sensors 240 (shown in FIG. 2) include detector elements 318 as discussed further below.

Gantry 302 and x-ray source 312 are controlled by monitoring and control system 200, which includes a gantry controller 336, an x-ray controller 338, a data acquisition system (DAS) 340, an image reconstructor 342, a conveyor controller 344, a gantry computer 346, a mass storage system 348, an operator console 350, and a display device 352. In some embodiments, gantry computer 346 is computer 105 (shown in FIGS. 1 and 2) and/or CPU 215 (shown in FIG. 2). Also, in some embodiments, mass storage system 348 is one of other devices 220 (shown in FIG. 2). Further, in some embodiments, operator console 350 is use input interface 130 (shown in FIG. 1). Moreover, is some embodiments, display device 352 is presentation interface 120 (shown in FIG. 1).

Gantry controller 336 controls the rotational speed and position of gantry 302, while x-ray controller 338 provides power and timing signals to x-ray source 312, and data acquisition system 340 acquires analog data from detector elements 318 and converts the data to digital form for subsequent processing. Image reconstructor 342 receives the digitized x-ray data from data acquisition system 340 and performs an image reconstruction process that involves filtering the projection data using a helical reconstruction algorithm.

Gantry computer 346 is in communication with gantry controller 336, x-ray controller 338, and conveyor controller 344 whereby control signals are sent from gantry computer 346 to controllers 336, 338, 344 and information is received from controllers 336, 338, 344 by gantry computer 346. Gantry computer 346 also provides commands and operational parameters to data acquisition system 340 and receives reconstructed image data from image reconstructor 342. The reconstructed image data is stored by gantry computer 346 in mass storage system 348 for subsequent retrieval. An operator (either first operator 230 or second operator 235, both shown in FIG. 2) interfaces with gantry computer 346 through operator console 350, which may include, for example, a keyboard and a graphical pointing device, and receives output, such as, for example, a reconstructed image, control settings and other information, on display device 352. Gantry computer 346 is a diagnostic computing device, i.e., in the exemplary embodiment, gantry computer 346 includes a diagnostic module 354, discussed further below.

Communication between the various system elements of FIG. 4 is depicted by arrowhead lines, which illustrate a means for either signal communication or mechanical operation, depending on the system element involved. Communication amongst and between the various system elements may be obtained through a hardwired or a wireless arrangement. Computer 346 may be a standalone computer or a network computer and may include instructions in a variety of computer languages for use on a variety of computer platforms and under a variety of operating systems. Other examples of computer 346 include a system having a microprocessor, microcontroller or other equivalent processing device capable of executing commands of computer readable data or program for executing a control algorithm. In order to perform the prescribed functions and desired processing, as well as the associated computations, e.g., the execution of Fourier analysis algorithm(s) and the control processes prescribed herein, computer 346 includes, without limitation, a processor(s) 115 and memory 110 (both shown in FIG. 1), storage, register(s), timing, interrupt(s), communication interfaces, and input/output signal interfaces, as well as combinations including at least one of the foregoing. For example, computer 346 may include input signal filtering to enable accurate sampling and conversion or acquisitions of such signals from communications interfaces. As described herein, exemplary embodiments are implemented through computer-implemented processes and apparatuses for practicing those processes.

Figure 5:
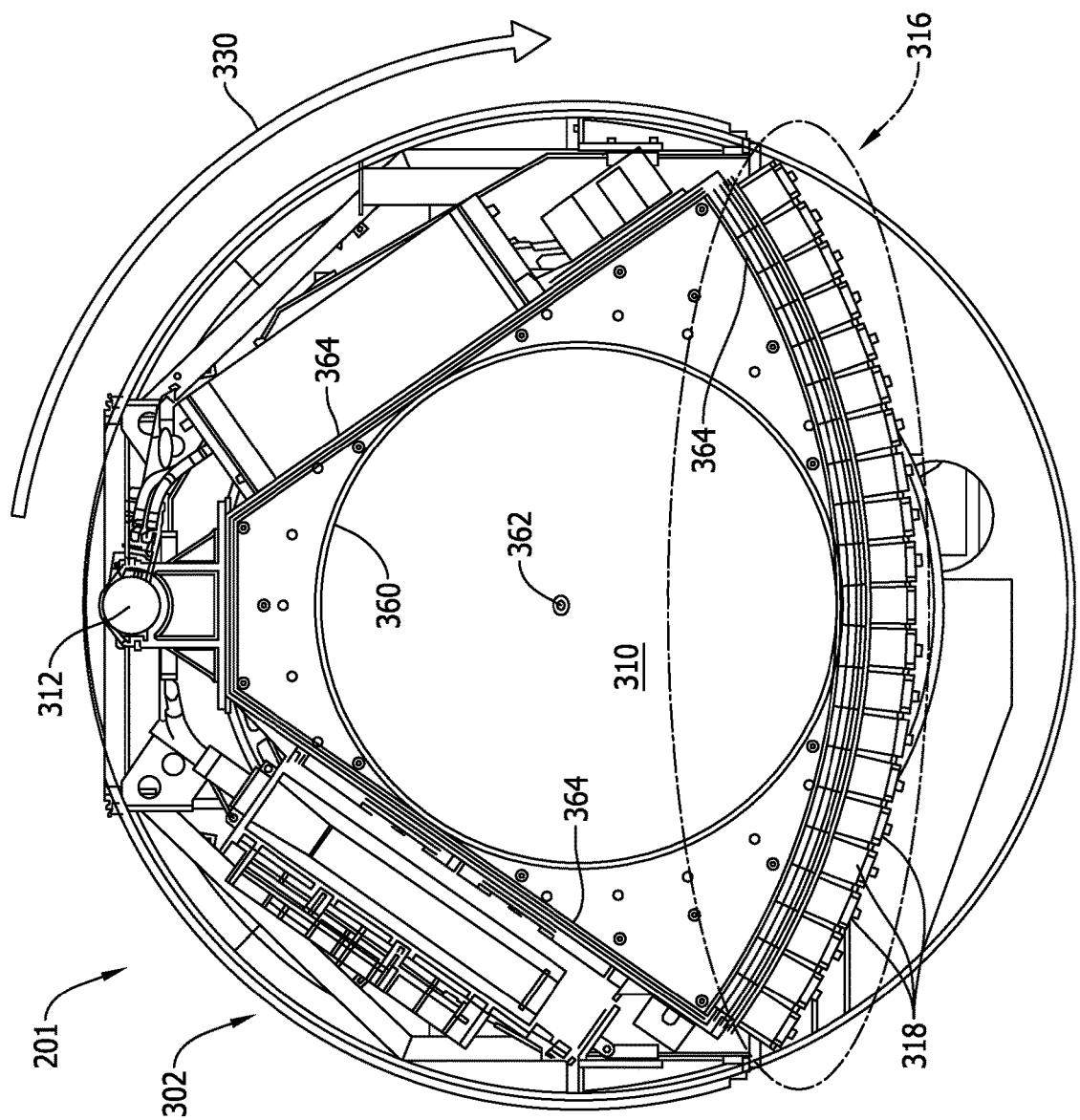

FIG. 5 is a schematic front view of rotatable gantry 302 that is used with CT imaging system 201. Gantry 302 includes x-ray source 312 and opposing detector array 316 with radiation detector elements 318. Radiation detector elements 318 use an array of photodiodes (not shown) to detect incident radiation. The photodiodes are naturally sensitive to photons in the optical, i.e., human-visible, range of the electromagnetic radiation spectrum. Therefore, higher-energy radiation, such as x-rays, is converted to optical photons through a scintillator for detection by the photodiodes, i.e., indirect detection detectors. Alternatively, photodiodes that absorb and detect higher-energy photons such as x-rays and gamma rays, i.e., direct detection detectors, are used. The methods described herein are applicable to both indirect and direct detection detectors. Photons, either directly as x-rays, or in the optical range originating as x-rays and being converted to photons in the optical range, once received by the photodiode, facilitate generation of signals that are used to generate images of the object being imaged.

Gantry 302 also includes a gantry support bearing 360 that facilitates rotation 330 of gantry 302 about a gantry rotational axis 362. In the exemplary embodiment, bearing 360 is a roller ball bearing that is approximately one meter in diameter. Alternatively, bearing 360 is any bearing that enables operation of CT imaging system 201 as described herein. Gantry bearing 360 is coupled to detector array 316 and the remainder of gantry 302 through a plurality of gantry bearing frame members 364. Detector array 316 and the associated gantry nearing frame member 364 at least partially define a mechanical diagnostic system of gantry bearing 360.

Figure 6:
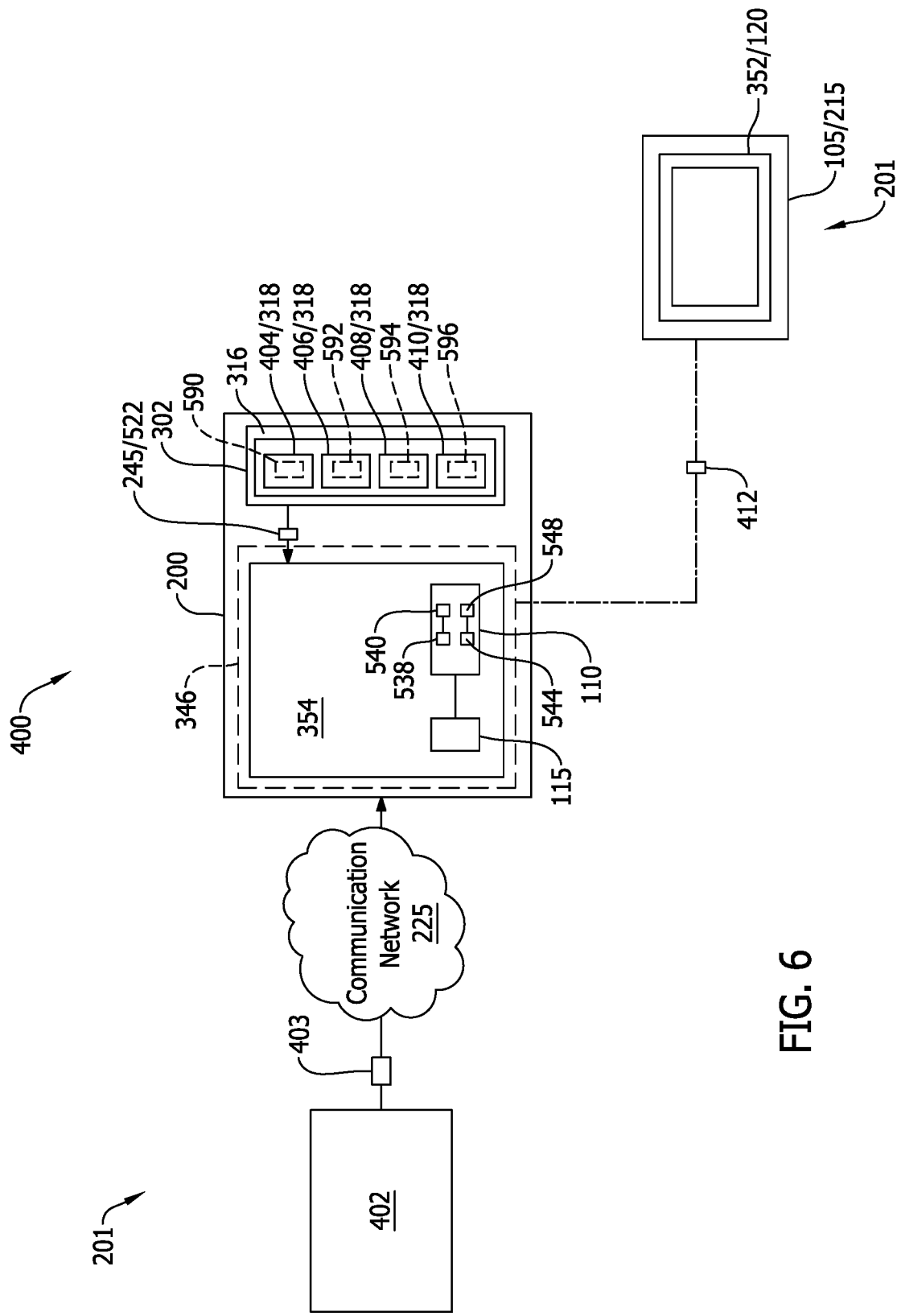

FIG. 6 is a schematic diagram of an exemplary diagnostic system 400 for CT imaging system 201 integrated with monitoring and control system 200. In the exemplary embodiment, diagnostic system 400 includes elements of CT imaging system 201, including elements of monitoring and control system 200. Therefore, diagnostic system 400 utilizes existing hardware and is substantially a computer-implemented retrofit upgrade. Diagnostic system 400 is used to capture data from individual detector elements 318 of detector array 316 to perform a diagnostic to determine a mechanical health of particular components, e.g., gantry bearing 360. Other components of rotatable gantry 302 may also be diagnosed using system 400, e.g., and without limitation, gantry bearing frame members 364, the gantry casing (not shown), and the gantry drive motor (not shown).

In the exemplary embodiment, diagnostic system 400 includes an update server 402 that is one of a stand-alone computing device 105 (shown in FIGS. 1 and 2), CPU 215 (shown in FIG. 2), and a remote server 220 as a portion of other devices 220 (shown in FIG. 2). Update server 402 is coupled to diagnostic module 354 that is embedded within gantry computer 346, through any combination of software, hardware, and firmware that enables diagnostic module 354 and diagnostic system 400 to operate as described herein. Update server 402 is coupled to diagnostic module 354 through a communications network 225, e.g., and without limitation, the Internet, a WAN, and a LAN. Diagnostic module 354 includes a processing device 115 coupled to a memory device 110. Update server 402 transmits update data 403 associated with rotatable gantry 302 and radiation detector elements 318, e.g., and without limitation, the respective offset currents (discussed further below).

Also, in the exemplary embodiment, diagnostic system 400 includes detector array 316. Detector array 316 includes the plurality of radiation detector elements 318, only four shown in FIG. 6, i.e., a first radiation detector element 404, a first radiation detector element 406, a third radiation detector element 408, and a fourth radiation detector element 410. Each of elements 318, 404, 406, 408, and 410 is further configured to generate electrical signals representing measurement data associated with the CT component being monitored, e.g., gantry bearing 360 (shown in FIG. 5).

Further, in the exemplary embodiment, diagnostic system 400 includes a client computing device 105/215 that includes output device 352/120 coupled to diagnostic module 354. Client computing device 105/215 receives status data 412 from gantry computer 346, where the status data is associated with radiation detector elements 318 (described in more details below).

Figure 7:
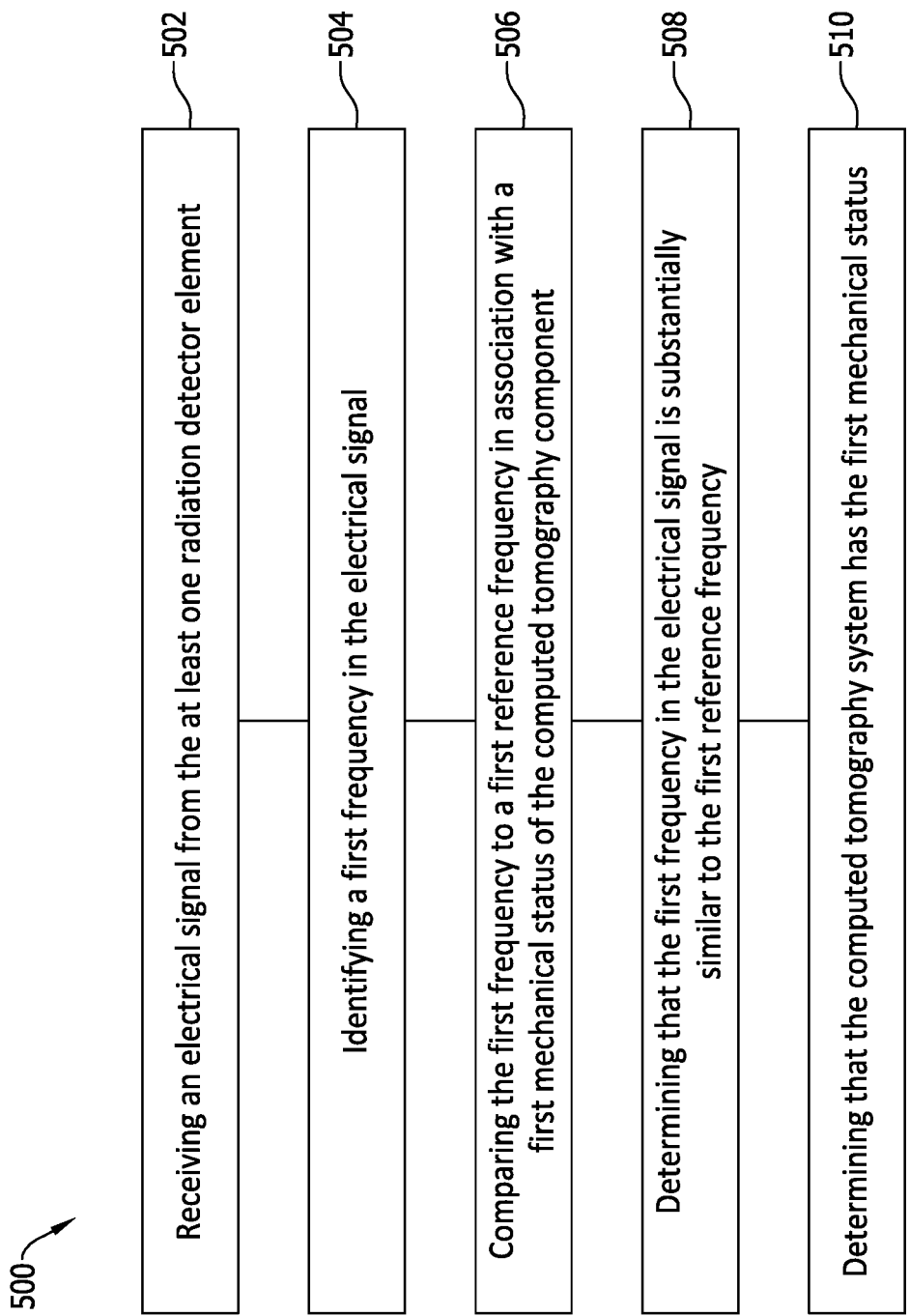
Figure 8:
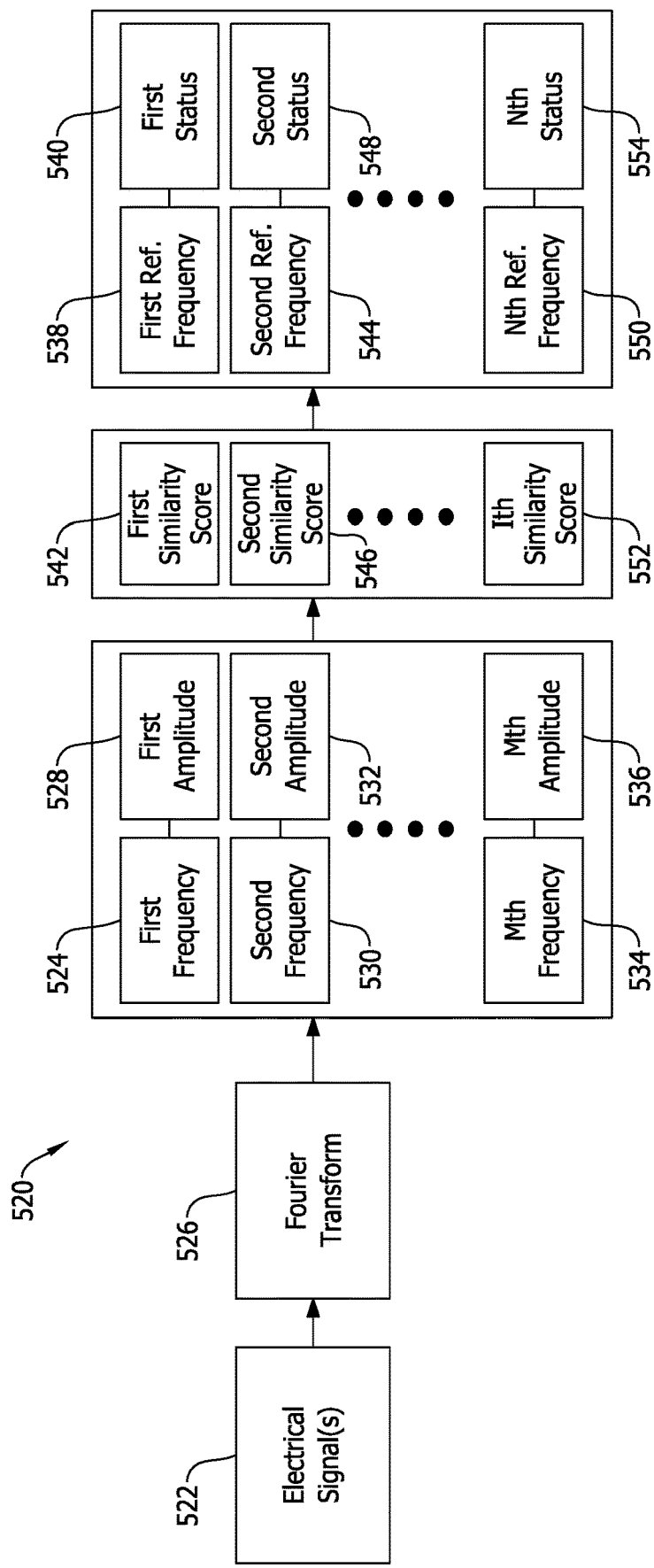

FIG. 7 is an exemplary method 500 of monitoring CT imaging system 201 (shown in FIGS. 3 and 4) with monitoring and control system 200 shown in FIGS. 2 and 4), specifically with diagnostic system 400 (shown in FIG. 6). FIG. 8 is a flow chart of an exemplary process 520 used to implement method 500 using diagnostic system 400. Referring to FIGS. 1-8, method 500 includes receiving 502, by diagnostic system 400, electrical signals 522 from at least one radiation detector element 318. Each Electrical signal 522 is substantially representative of an "offset current" generated and transmitted from a radiation detector element 318, and, electrical signals 522 include a change in the offset current associated with each radiation detector element 318.

In the exemplary embodiment, each of radiation detector elements 318 includes a number of photodiodes (not shown). The photodiodes have a "depletion region" that defines an energy gap, i.e., a barrier to electron flow through the photodiodes. This energy gap across which electrons must jump at steady-state is referred to as the "band gap" because electrons are known to have discreet potential energy levels (relative to an atom) called bands and the band gap is the difference in potential energy between the top valence band, i.e., the greatest potential energy, and the bottom, lowest potential energy, condition band once steady-state is achieved.

Electrons can gain potential energy through thermal effects. Specifically, an electron's potential energy (energy band) can be raised by absorbing thermal energy. At higher temperatures, i.e., non-zero Kelvin temperatures, these thermally-excited electrons "spontaneously" jump the band gap. This process is a random process dependent on the temperature in the photodiode and leads to a small current flowing through the diode when it is connected to a wider circuit. As such, the photodiodes are subject to a thermal current, typically referred to as a "dark current" or "offset current" since it is the current flowing, i.e., trickling through the photodiode even when the photodiode is not subjected to optical photons, i.e., is in complete darkness. This trickle current is viewed as an offset value that must be subtracted from whatever signal the photodiode creates under imaging conditions to obtain the accurate signal value. The subtraction of the offset current is typically called an "offset correction" and will be discussed further below. Increased temperature leads to an increased "thermal current". Also, decreasing and increasing the width of the band gap induces increased and decreased, respectively, thermal noise levels at fixed temperatures.

Mechanical strain defines a change in length of the object subjected to such strain. Such mechanical strains are induced by compressive and expansive stresses, i.e., forces through a well-established relationship. These stresses are induced by components mechanically coupled to radiation detector elements 318, e.g., gantry bearing 360. The photodiodes of elements 318 have a known area on which the induced forces act to define the stresses induced within the photodiodes. The expansions and contractions of the photodiodes are also experienced through the depletion regions therein. As such, expanding the depletion region decreases the band gap and compressing the depletion region increases the band gap. In the absence of a light signal, this change in the band gap leads to small changes in the offset current. Therefore, changes in the forces induced on detectors 318 through changes in the mechanical state of the mechanically coupled components of rotatable gantry 302 are measurable through the change in the measured offset current. Furthermore, since the relationship between the changes in offset current and the forces associated with the mechanical components of rotatable gantry 302 are understood, detectors 318 facilitate monitoring of the mechanical condition of such mechanical components and diagnosis of malfunctions thereof. Specifically, each radiation detector element 318 is used as a mechanical transducer. The transducer effect is then be used to identify frequency-dependent forces detector element 318 experiences either by its movement through space, or that it absorbs from the substantially rigid structure of rotatable gantry 302 as it rotates through space. These frequency-dependent forces are then used to identify various bearing defects, system imbalance, as well as create an independent estimate of gantry rotation speed for pitch calibration, among other determinations, and as discussed further below.

Figure 9:
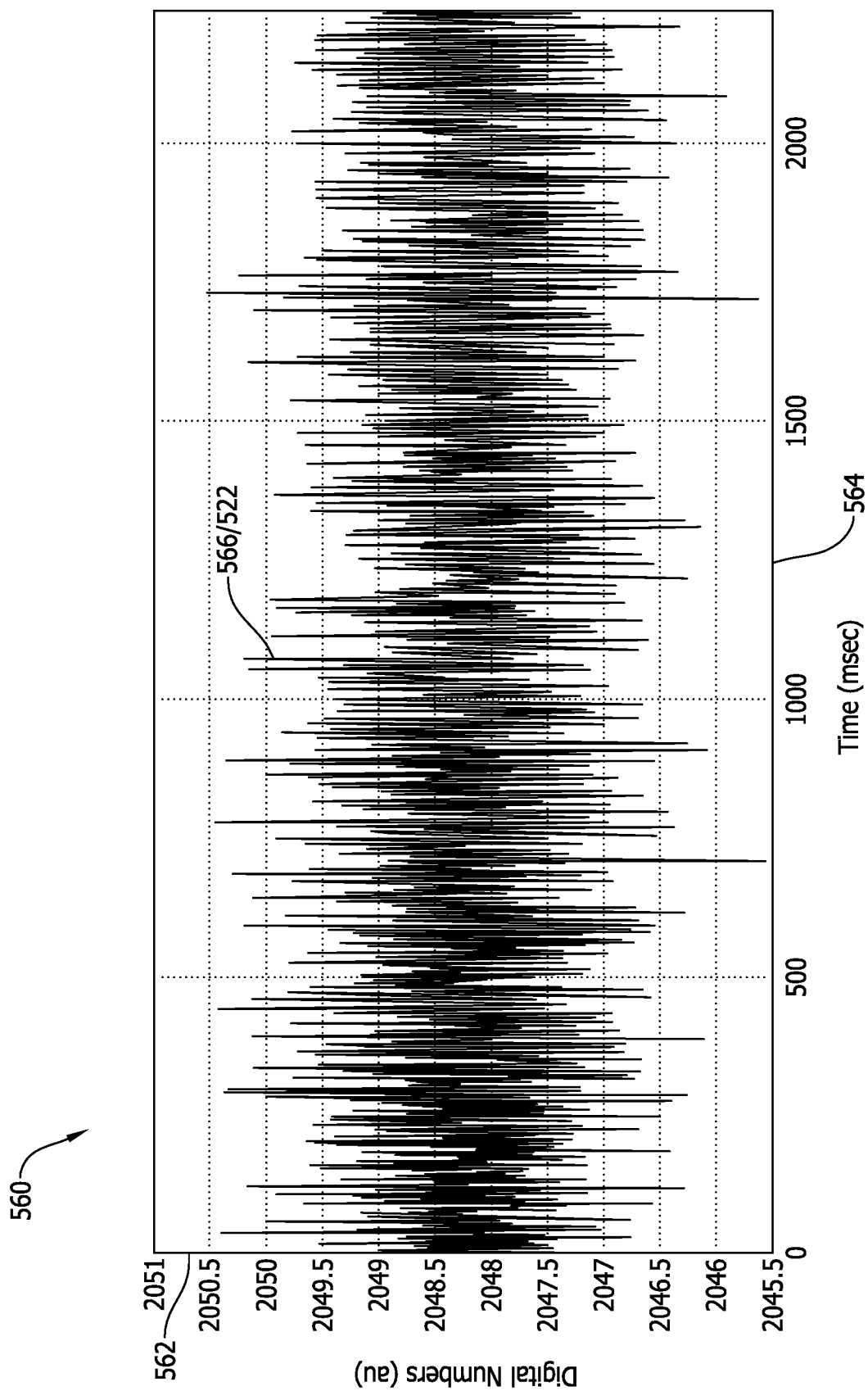

FIG. 9 is a graphical representation, i.e., graph 560 of raw offset data in the time domain received from one radiation detector element 318 (shown in FIGS. 4-6) of CT imaging system 201 (shown in FIGS. 3 and 5). Graph 560 includes an ordinate, i.e., y-axis 562 that represents a digital number in arbitrary units (au) that further represents an amplitude of a vibration signal from the particular radiation detector element 318, similar to that of an accelerometer. Y-axis 562 includes values that extend from 2045.5 au to 2051 au in increments of 0.5 au. Graph 560 also includes an abscissa, i.e., x-axis 564 that represents time in milliseconds (msec). X-axis 564 includes values that extend from 0 msec to approximately 2500 msec in increments of 500 msec. A raw trace 566 representative of electrical signal 522 is generated, where electrical signal 522 is representative of the offset current generated by and transmitted from a radiation detector element 318. As is typical of such vibration traces in the time domain, signal 522 as represented on trace 566 appears as random noise.

Referring again to FIGS. 1-8, method 500 also includes identifying 504, with diagnostic system 400, a first frequency 524 in electrical signal 522 through execution of Fourier analysis algorithm(s) 526, thereby determining a magnitude, i.e., first amplitude 528 of the acceleration at first frequency 524 through Fourier transform 526 on electrical signal 522. First frequency 524 and first amplitude 528 are based on signals 522 transmitted from all of radiation detector elements 318.

Figure 10:
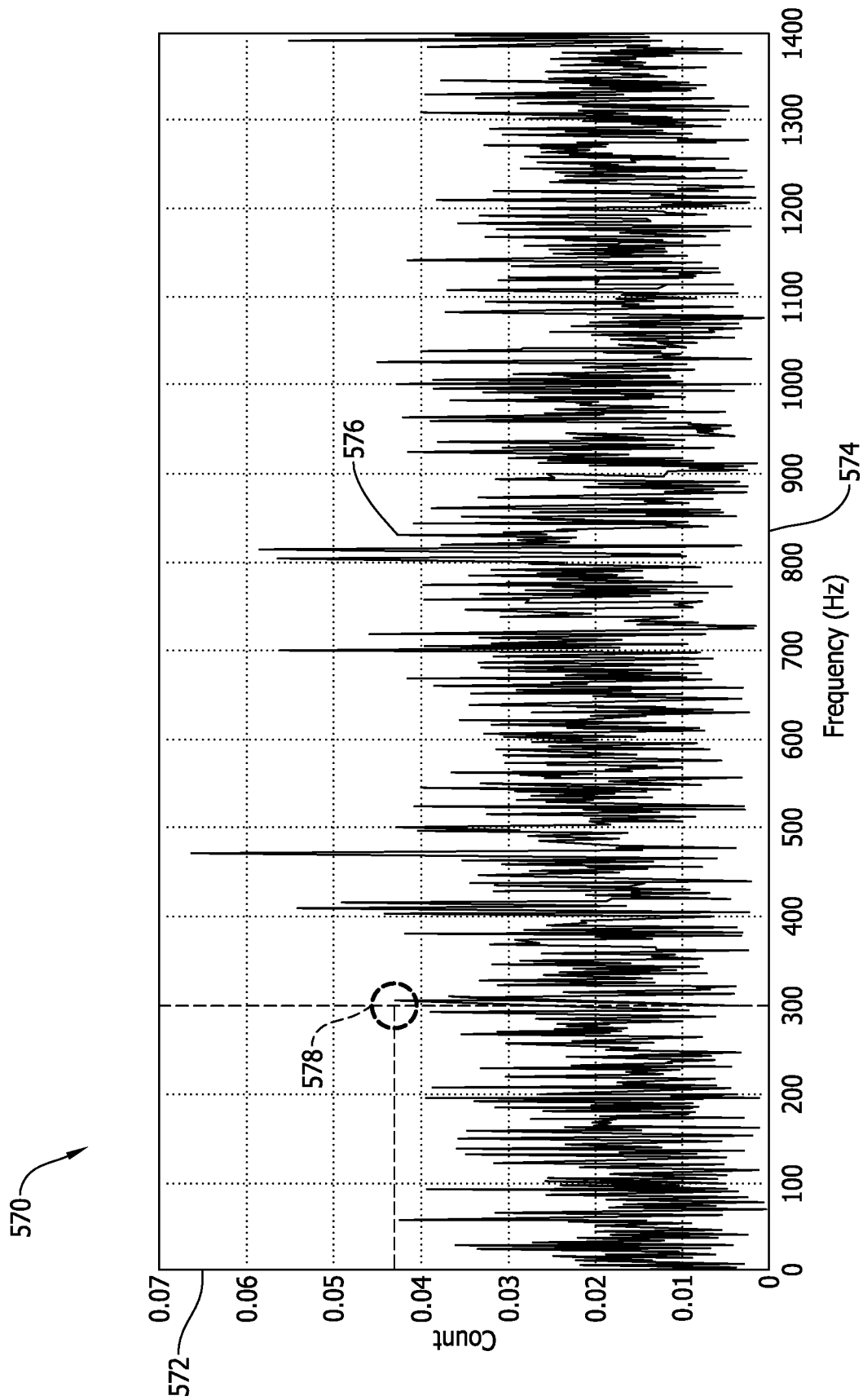

FIG. 10 is a graphical representation, i.e., graph 570 of raw vibration data 566 (shown in FIG. 9) transformed from the time domain into the frequency domain through Fourier transform 526. Graph 570 includes an ordinate, i.e., y-axis 572 that represents acceleration in units of counts per second received from the particular radiation detector element 318 (shown in FIGS. 4-6) for a particular frequency. Y-axis 572 includes values that extend from 0 counts per second to 0.07 counts per second in increments of 0.01 counts per second. Graph 570 also includes an abscissa, i.e., x-axis 574 that represents frequency in Hertz (Hz). X-axis 574 includes values that extend from 0 Hz to 1400 Hz in increments of 100 Hz. A transformed trace 576 representative of transformed trace 566 is generated. As is typical of such vibration traces in the frequency domain, some peaks shown in trace 576 are indicative of a stress acting on radiation detector element 318 and the magnitude of the peak is proportional to the magnitude of the stress; other peaks are due to electrical noise. Most of such peaks are either inherent to the particular detector element 318 or are of unknown origin and are not indicative of a malfunctioning component. However, rotatable gantry 302 is well-understood and there are known peaks at certain frequencies corresponding to known defects. As such, certain peaks of trace 576 are useful in providing indications of a mechanical state of components of rotatable gantry 302. For example, and without limitation, a peak 578 at approximately 300 Hz is indicative of a ball pass frequency, i.e., the frequency of when a rolling elements (not shown) of gantry bearing 360 rolls across a defect in either the inner race or the outer race (neither shown) of bearing 360. Therefore, in this example, first frequency 524 (shown in FIG. 8) is approximately 300 Hz and first amplitude 528 (shown in FIG. 8) is approximately 0.42 counts per second.

Referring again to FIGS. 1-8, a second frequency 530 and a second amplitude 532 are determined as described above from signals 522 transmitted from second radiation detector element 406. Similarly, a $M^{th}$ frequency 534 and a $M^{th}$ amplitude 536 are determined as described above from signals 522 transmitted from a $M^{th}$ radiation detector element.

Figure 11:
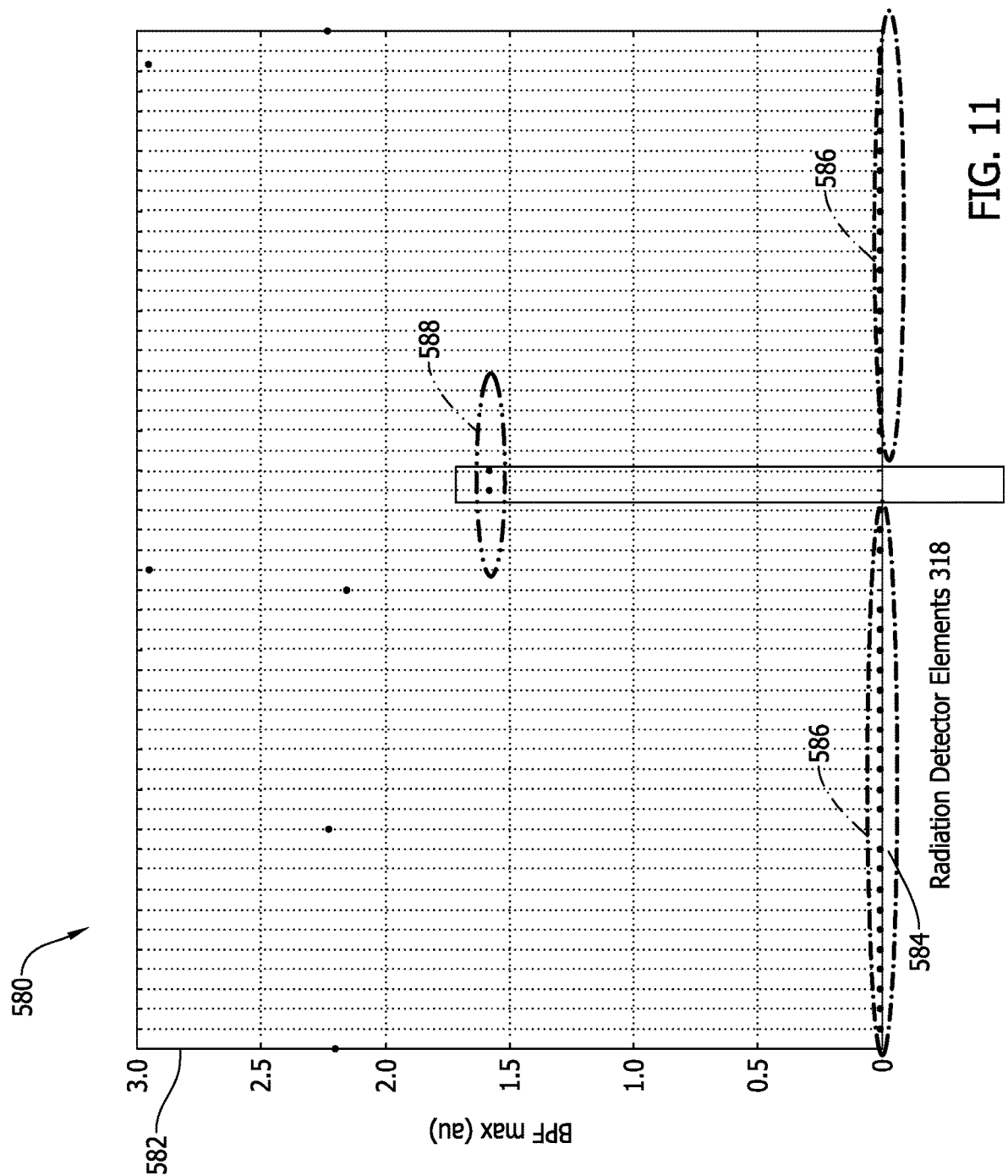

FIG. 11 is a graphical representation, i.e., graph 580 of a plurality of indications from radiation detector elements 318 (shown in FIGS. 4-6) found in a fleet of CT imaging system 201 (shown in FIGS. 3 and 5). Graph 580 includes an ordinate, i.e., y-axis 582 that represents the magnitude of the peak at the maximum measured ball pass frequency ($BPF_{max}$) as root mean squared values in arbitrary units (au) as received from the particular radiation detector element 318. Y-axis 582 includes values that extend from 0 to 3.0 in increments of 0.05. Graph 580 also includes an abscissa, i.e., x-axis 584 that represents each of several CT scanners in the fleet each containing detectors 318. As shown in FIG. 11, there are two distinct populations of indications. The majority of indications are negative indication 586. However, some indications are positive indications 588 (only two adjacent positive indications highlighted from the same CT scanner but at different times) that imply a defect in one of the races of gantry bearing 360 (shown in 5).

Referring again to FIGS. 1-8, method 500 further includes comparing 506, with diagnostic system 400, first frequency 524 in electrical signal 522 to a first reference frequency 538 stored in memory device 110, where first reference frequency 528 is at least partially indicative of a first mechanical status 540 of the CT component, i.e., gantry bearing 360. Method 500 also includes determining 508, with diagnostic system 400, that first frequency 524 in electrical signal 522 is substantially similar to first reference frequency 538 through determining a first similarity score 542. Method 500 also includes, in response to determining 508 that first frequency 524 is substantially similar to first reference frequency 538, determining 510, with diagnostic system 400, that CT imaging system 201 has first mechanical status 540.

For example, in the case of a race defect at approximately 300 Hz, the first reference frequency will be 300 Hz, the first frequency will be about 300 Hz, and the first similarity score will be about 0, thereby indicating that first status 540, i.e., a race defect is identified. First similarity score 542 may be a numerical value, a range, or a qualitative value.

Similarly, second frequency 530 is compared to a second reference frequency 544 to determine a second similarity score 546 and then determine a second mechanical status 548. $M^{th}$ frequency 534 is compared to a $N^{th}$ reference frequency 550 to determine an $i^{th}$ similarity score 552 to determine an $N^{th}$ mechanical status.

As discussed above, where the CT component monitored is gantry bearing 360, determining 510 that CT imaging system 201 has first mechanical status 540 includes determining, with diagnostic system 400, that gantry bearing 360 is defective based on first frequency 524 in electrical signals 522. Such defects as first status 540, second status 548, and $N^{th}$ status 554 may include, without limitation, race defects, roller defects, and a mass unbalance within rotatable gantry 302. Similar defect determinations may be made with second frequency 530 up to $M^{th}$ frequency 534.

Referring to FIGS. 6 and 8, diagnostic system 400 is further configured to calculate a first stress 590 on first radiation detector element 404 by applying a predefined conversion factor to first magnitude 528 of first frequency 524. Similar operations are performed to determine a second stress 592 on second radiation detector element 406, a third stress 594 on third radiation detector element 408, a fourth stress 596 on fourth radiation detector element 410, and so on for the full suite of radiation detector elements 318.

Referring to FIG. 8, diagnostic system 400 (shown in FIG. 6) is configured to perform an offset scan each radiation detector element 318 (shown in FIGS. 4-6) on CT imaging system 201 (shown in FIGS. 2-4 and 6). Such an offset scan is part of the calibration process of CT imaging system 201. The data collected during the offset scan is used as described above to determine the offset currents for each radiation detector element 318. These calibrations are typically performed every day and are performed in situ, i.e., they are performed where CT imaging system 201 is located and not just once at the factory prior to shipping. In general, such an offset scan is performed by taking data of electrical signals 522 when the x-rays are not being produced. Each individual radiation detector element 318 will have a different measured thermal current. In some embodiments, each different offset current is used in diagnostic system 400. In other embodiments, an average value of the offset currents is obtained and that value is used for all of detector elements 318.

Continuing to refer to FIG. 8, diagnostic system 400 may also be used to calculate a speed of rotation of rotatable gantry 302 (shown in FIGS. 3-6) based on first frequency 524 in electrical signals 522. Such a determination facilitates speed control of gantry 302 through determining an estimate of gantry speed as a feedback signal (not shown) to be used in a gantry speed control scheme (not shown). For example, a peak frequency, e.g., 2.5 Hz can be selected to represent a gantry speed of approximately 150 revolutions per minute (rpm) and the relationship between peak frequency and gantry speed is linear.

The embodiments described herein provide a cost-effective system and method for improving diagnostics of mechanical devices within computed tomography (CT) imaging systems. The systems and methods described herein use a diagnostic system for monitoring a mechanical status, e.g., bearing vibration of a CT imaging system using a plurality of radiation detector elements that are already installed and used for detecting the x-rays that will be used for imaging. In some implementations, the diagnostic system is configured to determine that the CT imaging system may have a defective bearing. Also, in some implementations, the diagnostic system is further configured to determine a mass imbalance associated with the rotatable gantry. Additionally, in some implementations, the diagnostic system is further configured to perform an offset scan, for example a periodic calibration scan. In some implementations, the diagnostic system is configured to calculate a speed of rotation of the rotatable gantry. Further, in some implementations, the diagnostic system is further configured to detect a change in an offset current associated with the each of the radiation detector elements. Moreover, in some implementations, the diagnostic system is further configured to determine a magnitude of the first frequency and calculate a stress on each radiation detector element. Since the embodiments described herein are substantially software-based, the software may be retroactively deployed on existing CT imaging systems. Therefore, the utilization of the current hardware configuration saves a substantial amount of time and expense in the retrofit activities. In addition, the embodiments described herein facilitate diagnostic monitoring such that maintenance schedules may be adjusted based on the material condition data obtained. For example, little to no change in bearing vibration signatures over a predetermined period of time facilitates postponing costly maintenance activities.

A technical effect of the systems and methods described herein includes at least one of: (a) dual-tasking of existing x-ray detector units in CT imaging systems with x-ray detection and mechanical condition monitoring; (b) facilitating early detection of a defective bearing based on measurements taken by the x-ray detector units; (c) more consistent monitoring of a gantry bearing during operation for the service life of the bearing; (d) determine a mass imbalance associated with a rotating CT imaging system gantry; (e) facilitate, using the radiation detector elements, a CT imaging system offset scan, for example, a periodic calibration scan; (f) facilitate, using the radiation detector elements, calculating a speed of rotation of the rotatable gantry; (g) detecting a change in an offset current associated with the each of the radiation detector elements; (h) determining a stress on each radiation detector element; (i) facilitating ease and lower costs of retrofit upgrades to existing CT imaging systems through minimal changes to the CT imaging system hardware with a software-based implementation; and (j) using material condition data of the gantry bearing to shift corrective and preventative maintenance activities either earlier or later.

Exemplary embodiments of CT imaging systems, and methods of operating such systems and devices are not limited to the specific embodiments described herein, but rather, components of systems and/or steps of the methods may be utilized independently and separately from other components and/or steps described herein. For example, the methods may also be used in combination with other x-ray imaging systems that use rapidly rotating components requiring bearing support, and are not limited to practice with only the CT imaging systems and methods as described herein. Rather, the exemplary embodiment can be implemented and utilized in connection with other imaging systems.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A diagnostic system for monitoring a status of a computed tomography (CT) system, said diagnostic system comprising:
    at least one radiation detector element configured to monitor a CT component and generate signals representing measurement data associated with the CT component; and
    a diagnostic computer device comprising a processor and a memory coupled to said processor, said diagnostic computer device in communication with said at least one radiation detector element, said diagnostic computer device configured to:
        receive an electrical signal from said at least one radiation detector element;
        identify a first frequency in the electrical signal;
        compare the first frequency in the electrical signal to a first reference frequency stored in said memory device, the first reference frequency at least partially indicative of a first mechanical status of the CT component;
        determine that the first frequency in the electrical signal is substantially similar to the first reference frequency; and
        in response to determining that the first frequency is substantially similar to the first reference frequency, determine that the CT system has the first mechanical status.

2. The diagnostic system in accordance with claim 1, wherein the CT component is a gantry bearing, said diagnostic computer device further configured to determine that the gantry bearing is defective based on the first frequency in the electrical signal.

3. The diagnostic system in accordance with claim 1, wherein the CT component is a rotatable gantry, said diagnostic computer device further configured to determine a mass imbalance associated with the rotatable gantry based on the first frequency in the electrical signal.

4. The diagnostic system in accordance with claim 1, wherein said diagnostic computer device is further configured to receive the electrical signal from said at least one radiation detector element when the CT system is performing an offset scan.

5. The diagnostic system in accordance with claim 1, wherein the CT component is a rotatable gantry, said diagnostic computer device further configured to calculate a speed of rotation of the rotatable gantry based on the first frequency in the electrical signal.

6. The diagnostic system in accordance with claim 1, wherein said diagnostic computer device is further configured to detect a change in an offset current associated with said at least one radiation detector element.

7. The diagnostic system in accordance with claim 1, wherein said diagnostic computer device is further configured to:
    determine a magnitude of the first frequency through a Fourier transform on the electrical signal; and
    calculate a stress on said at least one radiation detector element by applying a predefined conversion factor to the magnitude of the first frequency.

8. The diagnostic system in accordance with claim 1, wherein the first reference frequency is one of a plurality of reference frequencies stored in said memory device, said diagnostic computer device further configured to determine a respective level of similarity between the first frequency and each reference frequency of the plurality of reference frequencies.

9. The diagnostic system in accordance with claim 1, wherein said at least one radiation detector element comprises at least a first radiation detector element and a second radiation detector element, said diagnostic computer device further configured to determine a first stress acting on said first radiation detector element and a second stress acting on said second radiation detector element.

10. A computed tomography (CT) system comprising:
    a gantry configured to rotate, said gantry comprising:
        at least one gantry bearing frame member; and
        a gantry bearing coupled to said at least one gantry bearing frame member;
    at least one radiation detector element coupled to said at least one gantry bearing frame member, said at least one radiation detector element configured to monitor said gantry bearing and generate signals representing measurement data associated with said gantry bearing; and
    a diagnostic computer device comprising a processor and a memory coupled to said processor, said diagnostic computer device in communication with said at least one radiation detector element, said diagnostic computer device configured to:
        receive an electrical signal from said at least one radiation detector element;
        identify a first frequency in the electrical signal;
        compare the first frequency in the electrical signal to a first reference frequency stored in said memory device, the first reference frequency at least partially indicative of a first mechanical status of said gantry bearing;
        determine that the first frequency in the electrical signal is substantially similar to the first reference frequency; and
        in response to determining that the first frequency is substantially similar to the first reference frequency, determine that said CT system has the first mechanical status.

11. The CT system in accordance with claim 10, wherein said diagnostic computer device is further configured to determine that said gantry bearing is defective based on the first frequency in the electrical signal.

12. The CT system in accordance with claim 10, wherein said diagnostic computer device is further configured to determine a mass imbalance associated with said gantry based on the first frequency in the electrical signal.

13. The CT system in accordance with claim 10, wherein said diagnostic computer device is further configured to receive the electrical signal from said at least one radiation detector element when said CT system is performing an offset scan.

14. The CT system in accordance with claim 10, wherein said diagnostic computer device is further configured to calculate a speed of rotation of said gantry based on the first frequency in the electrical signal.

15. The CT system in accordance with claim 10, wherein said diagnostic computer device is further configured to detect a change in an offset current associated with said at least one radiation detector element.

16. The CT system in accordance with claim 10, wherein said diagnostic computer device is further configured to:
determine a magnitude of the first frequency through a Fourier transform on the electrical signal; and
calculate a stress on said at least one radiation detector element by applying a predefined conversion factor to the magnitude of the first frequency.

17. The CT system in accordance with claim 10, wherein the first reference frequency is one of a plurality of reference frequencies stored in said memory device, said diagnostic computer device further configured to determine a respective level of similarity between the first frequency and each reference frequency of the plurality of reference frequencies.

18. The CT system in accordance with claim 10, wherein said at least one radiation detector element comprises at least a first radiation detector element and a second radiation detector element, said diagnostic computer device further configured to determine a first stress acting on said first radiation detector element and a second stress acting on said second radiation detector element.

19. A method of monitoring a computed tomography (CT) system, the CT system including at least one CT component and a diagnostic system including at least one radiation detector element, the diagnostic system coupled to the at least one CT component, said method comprising:
receiving, by the diagnostic system, an electrical signal from the at least one radiation detector element;
identifying, with the diagnostic system, a first frequency in the electrical signal;
comparing, with the diagnostic system, the first frequency in the electrical signal to a first reference frequency stored in a memory device, the first reference frequency at least partially indicative of a first mechanical status of the at least of one CT component;
determining, with the diagnostic system, that the first frequency in the electrical signal is substantially similar to the first reference frequency; and
in response to determining that the first frequency is substantially similar to the first reference frequency, determining, with the diagnostic system, that the CT system has the first mechanical status.

20. The method in accordance with claim 19, wherein the CT component is a gantry bearing, wherein determining that the CT system has the first mechanical status comprises determining, with the diagnostic system, that the gantry bearing is defective based on the first frequency in the electrical signal.

21. The method in accordance with claim 19, wherein the CT component is a rotatable gantry, wherein determining that the CT system has the first mechanical status comprises determining, with the diagnostic system, a mass imbalance associated with the rotatable gantry based on the first frequency in the electrical signal.

22. The method in accordance with claim 19, wherein receiving an electrical signal from the at least one radiation detector element comprises performing an offset scan on the CT system.

23. The method in accordance with claim 19, wherein the CT component is a rotatable gantry, said method further comprising calculating, with the diagnostic system, a speed of rotation of the rotatable gantry based on the first frequency in the electrical signal.

24. The method in accordance with claim 19, wherein receiving an electrical signal from the at least one radiation detector element comprises detecting, with the diagnostic system, a change in an offset current associated with the at least one radiation detector element.

25. The method in accordance with claim 19 further comprising:
determining, with the diagnostic system, a magnitude of the first frequency through a Fourier transform on the electrical signal; and
calculating, with the diagnostic system, a stress on said at least one radiation detector element by applying a predefined conversion factor to the magnitude of the first frequency.

26. The method in accordance with claim 19, wherein the first reference frequency is one of a plurality of reference frequencies stored in the diagnostic system, said method further comprising determining, with the diagnostic system, a respective level of similarity between the first frequency and each reference frequency of the plurality of reference frequencies.

27. The method in accordance with claim 19, wherein the at least one radiation detector element includes at least a first radiation detector element and a second radiation detector element, said method further comprising determining, with the diagnostic system, a first stress acting on the first radiation detector element and a second stress acting on the second radiation detector element.

* * * * *